US00PP14414P39

(12) United States Plant Patent
Pieters

(10) Patent No.: US PP14,414 P3
(45) Date of Patent: Dec. 23, 2003

(54) CHRYSANTHEMUM PLANT NAMED 'GEDI TWO YLNOV'

(50) Latin Name: *Chrysanthemum morifolium*
Varietal Denomination: Gedi Two Ylnov

(75) Inventor: Dirk Pieters, Staden (BE)

(73) Assignee: Pieters Plant Production, BVBA, Oostnieuwkerke (BE)

( * ) Notice: Subject to any disclaimer, the term of this patent is extended or adjusted under 35 U.S.C. 154(b) by 0 days.

(21) Appl. No.: 10/137,792

(22) Filed: May 1, 2002

(65) Prior Publication Data

US 2003/0208812 P1 Nov. 6, 2003

(51) Int. Cl.[7] ..... A01H 5/00
(52) U.S. Cl. ..... Plt./289
(58) Field of Search ..... Plt./289, 287

(56) References Cited

U.S. PATENT DOCUMENTS

PP10,463 P 6/1998 Wain ..... Plt./289

OTHER PUBLICATIONS

Brummitt, Horticultural Science Chrysanthemum once again, The Garden, 1997, pp. 662–663.*

* cited by examiner

*Primary Examiner*—Bruce R. Campell
*Assistant Examiner*—June Hwu
(74) *Attorney, Agent, or Firm*—Knobbe, Martens, Olson & Bear, LLP

(57) ABSTRACT

A new and distinct Chrysanthemum plant cultivar is disclosed, characterized by a decorative-type inflorescence, consistent flowering response to short days, blooming consistently after 49 days of short day length, free branching habit, yellow ray florets, a very uniform round growth habit, and a large quantity of blooms per flowering branch.

1 Drawing Sheet

Latin name of the genus and species: The present invention relates to a new and distinct cultivar of Chrysanthemum plant, botanically known as *Chrysanthemum morifolium.*

Variety denomination: The new and distinct Chrysanthemum plant is hereinafter referred to by the cultivar name 'Gedi Two Ylnov.'

BACKGROUND OF THE INVENTION

The new cultivar is a natural mutation that occurred on a single branch of a plant of the Chrysanthemum cultivar 'Novare Orange' (undistributed in the United States). The new cultivar was discovered and asexually propagated by the inventor in October 1996.

Asexual reproduction of the new cultivar by apical tip cutting and meristem tissue culture was performed in Oxnard, Calif. and has shown that the unique features of this cultivar are stable and reproduced true to type on successive generations.

SUMMARY OF THE INVENTION

The cultivar 'Gedi Two Ylnov' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'Gedi Two Ylnov.' These characteristics in combination distinguish 'Gedi Two Ylnov' as a new and distinct Chrysanthemum cultivar:

1. Decorative-type inflorescence,
2. Consistent flowering response to short days, blooming consistently after 49 days of short day length, 3. Free branching habit,
4. Yellow ray florets,
5. Very uniform round growth habit, and
6. Large quantity of blooms per flowering branch.

Plants of the new cultivar are similar to plants of the parent cultivar, 'Novare Orange' in most horticultural characteristics, however plants of the new cultivar differed from plants of the cultivar 'Novare Orange' primarily in ray floret color. The inflorescences of the new cultivar also have a smaller diameter than those of the parent variety.

In comparison to the commercially available variety 'Cleagar GF 1' (U.S. Plant Pat. No. 10,463), 'Gedi Two Ylnov' has a more round plant shape and greater branching, more blooms per flowering branch, and a flatter inflorescence.

BRIEF DESCRIPTION OF THE PHOTOGRAPH

The photograph shows a plant of 'Gedi Two Ylnov' in a six-inch container. One cutting was used in the pot.

DETAILED BOTANICAL DESCRIPTION

In the following description, color references are made to The Royal Horticultural Society Colour Chart except where general terms of ordinary dictionary significance are used. The following observations and measurements describe plants grown in Oxnard, Calif. during the month of December and January. The age of the observed plants is 92 days from a rooted cutting. The growing temperature ranged from 55° to 68° F. at night to 60° to 75° F. during the day. Measurements and numerical values represent averages of typical flowering types.

Botanical classification: *Chrysanthemum morifolium* cultivar 'Gedi Two Ylnov'.

Commercial classification: Garden-type Chrysanthemum.
Parentage: Natural mutation of the Chrysanthemum cultivar 'Novare Orange' (Undistributed in the United States).

PROPAGATION

Time to rooting: 7 to 14 days at approximately 21° C.
Root description: Fine, fibrous.

PLANT

Growth habit: Mounding herbaceous perennial.
Height: Approximately 23 cm.
Spread: Approximately 24 cm.
Growth rate: Moderate.
Branching characteristics: Free Branching.
Length of lateral branches: Approximately 22.5 cm.
Number of leaves per lateral branch: Approximately 15.

FOLIAGE

Leaf:
- *Arrangement.*—Alternate.
- *Average length.*—Approximately 5.0 cm.
- *Average width.*—Approximately 3.4 cm.
- *Shape of blade.*— *Ovate.*
- *Apex.*—*Cuspidate.*
- *Base.*—Attenuate.
- *Attachment.*—Stalked.
- *Margin.*—Palmately lobed.
- *Texture of top surface.*—Lightly pubescent.
- *Texture of bottom surface.*—Lightly pubescent.
- *Color.*—Young foliage upper side: Near 135A. Young foliage under side: Near 137B. Mature foliage upper side: Near 139A. Mature foliage under side: Near 137C. Venation upper side: Near 138B. Venation under side: Near 138B.
- *Venation type.*—Palmately net.

Petiole:
- *Average length.*—Approximately 2.2 cm.
- *Color.*—Near 139A.
- *Diameter.*—Approximately 0.2 cm.

BLOOM

Inflorescence:
- *Flowering habit.*—Induced by darkness period greater than 13.5 hours, approximately 49 days of appropriate day length required to induce and develop blooms.
- *Inflorescence form.*—Decorative.
- *Natural flowering season.*—Approximately the middle two weeks of September.
- *Number of inflorescences per lateral branch.*—Approximately 20.
- *Inflorescence diameter.*—Approximately 3.5 cm.
- *Inflorescence depth.*—Approximately 1.2 cm.
- *Inflorescence longevity on plant.*—Approximately 16 days.
- *Persistence.*—Persistent.

Ray florets:
- *Appearance.*—Matte.
- *Texture.*—Smooth.
- *Average number per flower.*—159.
- *Shape.*—Oblanceolate.
- *Aspect.*—Approximately 30% of ray florets are cylindric in the bottom one-third of the floret and the upper two-thirds of the floret is cymbiform; approximately 65% of ray florets are completely cymbiform and deeply lobed; approximately 5% of the florets are cylindric.
- *Margin.*—Approximately 35% of the ray florets are entire; approximately 65% are deeply lobed.
- *Apex.*—Retuse.
- *Length.*—Approximately 1.4 cm.
- *Width.*—Approximately 0.4 cm.
- *Color.*—Upper surface at first opening: Near 9A. Upper surface at maturity: Near 7A. Upper surface at fading: Near 7B. Under surface at first opening: Near 6A. Under surface at maturity: Near 6B. Under surface at fading: Near 12A.

Disc florets:
- *Appearance.*—Shiny.
- *Texture.*—Smooth.
- *Average number per flower.*—Approximately 10.
- *Shape.*—Cylindric.
- *Apex.*—Obtuse.
- *Average length.*—Approximately 0.5 cm.
- *Average width.*—Approximately 0.1 cm.
- *Color.*—At first opening: Near 7C. At maturity: Near 16A. At fading: Near 16B.

Peduncle:
- *Length.*—At terminal end (shortest): Approximately 3.0 cm. At lateral end (longest): Approximately 6.8 cm.
- *Angle to stem.*—Acute.
- *Strength.*—Moderate.
- *Color.*—Near 138B.
- *Habit.*—Upright.
- *Diameter.*—Approximately 0.2 cm.
- *Surface texture.*—Lightly pubescent.

Inflorescence bud:
- *Length.*—Approximately 0.5 cm.
- *Diameter.*—Approximately 1 cm.
- *Form.*—Globular.
- *Color.*—Near 2B.

Involucral bracts (phyllaries):
- *Appearance.*—Matte.
- *Texture.*—Lightly pubescent.
- *Number.*—29.
- *Shape.*—Oblanceolate.
- *Margin.*—Entire.
- *Apex.*—Acute.
- *Length.*—Approximately 0.6 cm.
- *Width.*—Approximately 0.3 cm.
- *Color.*—Upper side: Near 143A. Under side: Near 143A.

REPRODUCTIVE ORGANS

Ray florets:
- *Number of pistils per flower.*—1.
- *Stigma shape.*—2 branched.
- *Stigma color.*—Near 2B.
- *Style color.*—Near 1C.
- *Style length.*—Approximately 0.4 cm.
- *Stamens.*—Absent.

Disc florets:
- *Number of pistils per flower.*—1.
- *Stigma shape.*—Two-branched.
- *Stigma color.*—Near 12B.
- *Style length.*—Approximately 0.3 cm.
- *Style color.*—Near 154D.
- *Number of stamens per flower.*—4.
- *Anther shape.*—Tubular.
- *Anther color.*—Near 13A.
- *Pollen color.*—Pollen is not present.

OTHER CHARACTERISTICS

Seed production: Commercially, this plant is not used or observed in a stage wherein seeds would be produced. Therefore, seed production has not been observed.

Disease resistance: Neither resistance nor susceptibility to diseases and pests has been observed in this cultivar.

Heat and cold resistance: Plants with flowers are hardy to low temperatures about −2° C. Non flowering plants are hardy in the approximate range of 3° C. to −6° C., depending upon duration of cold and amount of moisture in the soil. With adequate water plants are hardy to a high temperature of 49° C.

What is claimed is:

1. A new and distinct cultivar of Chrysanthemum plant named 'Gedi Two Ylnov' as herein illustrated and described.

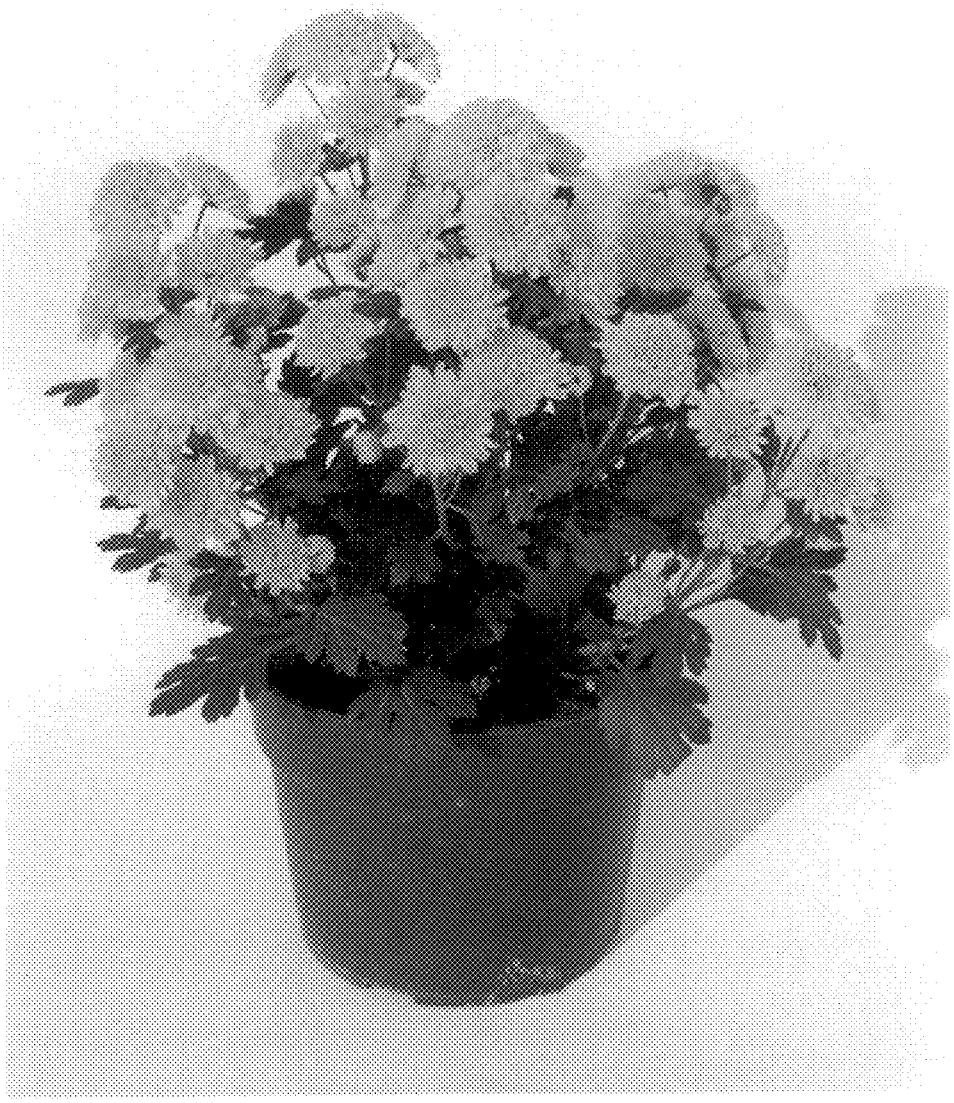

* * * * *